(12) United States Patent
Paul

(10) Patent No.: US 10,031,202 B2
(45) Date of Patent: Jul. 24, 2018

(54) METHOD AND MAGNETIC RESONANCE APPARATUS FOR THE ACQUISITION OF MR DATA OF A SLICE WITHIN A SUBJECT

(71) Applicant: Siemens Aktiengesellschaft, München (DE)

(72) Inventor: Dominik Paul, Bubenreuth (DE)

(73) Assignee: Siemens Aktiengesellschaft, Munich (DE)

(*) Notice: Subject to any disclaimer, the term of this patent is extended or adjusted under 35 U.S.C. 154(b) by 798 days.

(21) Appl. No.: 14/661,179

(22) Filed: Mar. 18, 2015

(65) Prior Publication Data

US 2015/0268322 A1 Sep. 24, 2015

(30) Foreign Application Priority Data

Mar. 18, 2014 (DE) .......................... 10 2014 205 004

(51) Int. Cl.
*G01R 33/561* (2006.01)
*G01R 33/565* (2006.01)
*A61B 5/055* (2006.01)
*G01R 33/34* (2006.01)
*G01R 33/48* (2006.01)

(52) U.S. Cl.
CPC ............ *G01R 33/561* (2013.01); *A61B 5/055* (2013.01); *G01R 33/34* (2013.01); *G01R 33/4818* (2013.01); *G01R 33/565* (2013.01); *G01R 33/482* (2013.01); *G01R 33/5617* (2013.01); *G01R 33/56536* (2013.01); *G01R 33/56563* (2013.01)

(58) Field of Classification Search
CPC .. G01R 33/561; G01R 33/34; G01R 33/4818; G01R 33/565; G01R 33/482; G01R 33/5617; G01R 33/56536; G01R 33/56563; A61B 5/055
USPC .......................................................... 324/309
See application file for complete search history.

(56) References Cited

U.S. PATENT DOCUMENTS

2010/0033179 A1 2/2010 Hargreaves et al.
2013/0278254 A1 10/2013 Reeder et al.

OTHER PUBLICATIONS

Lu et al: "SEMAC: Slice Encoding for Metal Artifact Correction in MRI", Magnetic Resonance in Medicine 62, pp. 66-76, (2009).

(Continued)

*Primary Examiner* — Melissa Koval
*Assistant Examiner* — Rahul Maini
(74) *Attorney, Agent, or Firm* — Schiff Hardin LLP

(57) ABSTRACT

In a method and magnetic resonance (MR) apparatus for acquisition of MR data from a slice in a subject, a first slice selection gradient is activated in a first direction perpendicular to the slice, and an RF excitation pulse then selectively excites nuclear spins in the slice. A second slice selection gradient is activated along the first direction, and a refocusing pulse is radiated. A first phase encoding gradient along the first direction is activated, and a second phase encoding gradient is activated along a second direction perpendicular to the first direction. A selection gradient is activated along a third direction perpendicularly to the first and second directions, during which MR data are acquired from the slice. The acquired MR data are entered into multiple k-space lines that are selected starting from the refocusing pulse, without a further RF pulse being radiated.

10 Claims, 6 Drawing Sheets

(56) References Cited

OTHER PUBLICATIONS

Sutter et al.., "Reduction of Metal Artifacts in Patients with Total Hip Arthroplasty with Slice-encoding Metal Artifact Correction and View-Angle Tilting MR Imaging"; Radiology; vol. 265; No. 1; pp. 204-214;(2012).

METHOD AND MAGNETIC RESONANCE APPARATUS FOR THE ACQUISITION OF MR DATA OF A SLICE WITHIN A SUBJECT

BACKGROUND OF THE INVENTION

Field of the Invention

The present invention relates to a method and to a magnetic resonance apparatus for acquiring MR data from a slice of a volume segment within an examination subject, in particular in the presence of magnetic field inhomogeneities.

Description of the Prior Art

In order to suppress metal artifacts in SE (Spin Echo)-based sequences (such as TSE (Turbo Spin Echo), for example), a SEMAC method can be used, see "SEMAC: Slice Encoding for Metal Artifact Correction in MRI", W. Lu et al., Magnetic Resonance In Medicine 62, pp. 66-76, 2009. This involves carrying out an additional coding in the direction of the slice while using a conventional two-dimensional protocol or slice-based scan. This coding corresponds to a phase coding and is also known as "SEMAC-encoding". With this method, the scanning time increases linearly with the number of additional phase coding steps in the slice selection direction, which are also referred to as SEMAC steps. In particular with T2-weighted TSE-protocols with a long repetition time TR, the entire scanning time clearly increases.

For example, to acquire a slice with 256 phase coding steps in a TSE-sequence with a turbofactor of 8 and a repetition time TR of 4 seconds, a scanning time of 2 minutes and 8 seconds is required. If eight SEMAC steps are used to suppress metal artifacts, the scanning time increases to over 17 minutes, which is clearly too long for clinical protocols.

SUMMARY OF THE INVENTION

The present invention therefore addresses the problem of reducing the scanning time compared with the prior art, and nevertheless suppressing metal artifacts.

In accordance with the present invention, a method is provided for the acquisition of MR data relating to an individual slice of a volume segment within an examination subject by operation of a magnetic resonance apparatus that includes the following steps in order to acquire the MR data in the slice:

Switching (activating) on a first slice selection gradient along a first direction or slice selection direction which is perpendicular to the slice.

Radiating an RF refocusing pulse to selectively excite the slice while the slice selection gradient is applied, such that only the spins in the slice are excited.

Applying a second slice selection gradient along the first direction.

Radiating an RF excitation pulse while the second slice selection gradient is applied, in order to refocus only the spins in the slice.

Applying a first phase-encoding gradient along the first direction. Applying this first phase-encoding gradient can also be referred to as SEMAC-encoding, such that the first phase-encoding gradient is used for the SEMAC-encoding, in particular.

Applying a second phase-encoding gradient along a second direction, which is perpendicular to the first direction.

Applying a selection gradient along a third direction, which is perpendicular to the first and second direction.

Selecting the MR data while the selection gradient is applied, wherein the MR data for a k-space line are selected.

In the inventive method, multiple k-space lines are selected, starting from the same RF refocusing pulse without a further RF pulse (for example, a further RF excitation pulse or a further refocusing pulse) being radiated. In other words, the relevant steps for selecting a slice (that is, applying a phase-encoding gradient, selecting the MR data) are carried out multiple times for the same refocusing pulse.

Since multiple k-space lines are selected for each refocusing pulse, the scanning time can be reduced. For example, for a scenario wherein four echoes are evaluated and thus four k-space lines are selected per refocusing pulse, the scanning time can be reduced by over a third overall.

Therefore, according to the invention, the scanning time is reduced by the use of multi-gradient echoes in a spin-echo sequence, a method which is similar to TGSE (Turbo Gradient Spin Echo). After the same refocusing pulse, multiple gradient-echoes are therefore selected.

To select multiple k-space lines starting from the refocusing pulse, there are a number of variants. According to a first variant, the following steps are carried out for the respective selection of one of these k-space lines:

The first phase-encoding gradient is applied along the first direction (that is, along the slice selection direction).

The selection gradient is applied along the third direction.

The MR data are acquired while the selection gradient is applied.

In this first variant, the second phase-encoding gradient is not changed during the selection of multiple k-space lines for the same refocusing pulse.

According to a second variant, for the respective selection of one of these k-space lines, the following steps are carried out:

The second phase-encoding gradient is applied along the second direction.

The selection gradient is applied along the third direction.

The MR data are acquired while the selection gradient is applied.

In this second variant, the first phase-encoding gradient is not changed during the selection of the multiple k-space lines for the same refocusing pulse.

According to the invention, multiple refocusing pulses can be radiated in each case for the same RF excitation pulse and multiple k-space lines can be selected for each of these refocusing pulses, without a further RF excitation pulse being radiated for this purpose.

While the effect of the previously applied phase-encoding gradient is virtually obliterated when the RF excitation pulse is radiated, this is not the case with the radiation of a refocusing pulse. Therefore, when radiating one of the refocusing pulses that do not correspond to the first pulse chronologically after the respective RF excitation pulse, the effect (that is, the gradient moment) of the previous gradient has to be taken into account. In order to take into account this effect of the gradient that was previously applied, there are two variants according to the invention.

According to the first variant, after the selection of the k-space lines for a specific one of the refocusing pulses and before the radiation of a further one of the refocusing pulses that chronologically comes directly after the designated refocusing pulse, a third phase-encoding gradient is applied along the first direction. With this third phase-encoding gradient, the effect of the gradients along the first direction that have been applied since the designated refocusing pulse is cancelled out. Similarly, before the radiation of the further refocusing pulse, a fourth phase-encoding gradient is applied along the second direction. With this fourth phase-encoding gradient, the effect of the gradients that have been applied since the designated refocusing pulse is cancelled out.

With the third or fourth phase-encoding gradient, a gradient moment is generated in each case, which corresponds in strength to a further gradient moment generated by those gradients (or generated by that gradient if only one gradient has been applied), which have (has) been applied along the first or along the second direction since the designated refocusing pulse. Since the gradient moment generated by the third or the fourth phase-encoding gradient is of opposite sign compared to the further gradient moment, the effect of the further gradient moment is reversed or cancelled out.

According to the second variant, after the selection of the k-space lines for a designated one of the refocusing pulses and after the radiating of a further one of the refocusing pulses that chronologically comes directly after the designated refocusing pulse, the effect of the gradients along the first direction that have been applied between the chronologically last RF excitation pulse and the further refocusing pulse is taken into account when applying the first phase-encoding gradient that chronologically comes directly after the further refocusing pulse. In a similar manner, in the second variant, when applying the second phase-encoding gradient, which is applied directly after the further refocusing pulse, the effect of the gradients along the second direction that have been applied between the last RF-excitation pulse and the further refocusing pulse is taken into account.

In the first variant, the further gradient moment generated by those gradients along the first or second direction that have been applied chronologically between the designated refocusing pulse and the further refocusing pulse is virtually cancelled out or eliminated by the gradient moment generated by the third or fourth phase-encoding gradient. As a result, the first or second phase-encoding gradient that is applied chronologically directly after the further refocusing pulse does not have to take into account any gradient moments (that is, any effect of previous gradients). Conversely, in the second variant, in order to generate the effect targeted by the first or second phase-encoding gradient (that is, the resulting target gradient moment), the first or second phase-encoding gradient that is applied chronologically directly after the further refocusing pulse has to take into account the (non-reversed) gradient moment that has been generated by the gradients applied chronologically earlier, since the last RF-excitation pulse.

In the following, it is assumed that the gradients that have been applied along the first (second) direction since the last RF excitation pulse was radiated have, at the time when the further refocusing pulse was radiated, generated in total the further gradient moment $Gm_{alt}$. It is further assumed that the first (second) phase-encoding gradient that is to be applied chronologically directly after the further refocusing pulse is intended to ensure that a gradient moment $Gm_{soll}$ is present after said gradient has been applied. Then the first (second) phase-encoding gradient has to generate a gradient moment $GM_{neu}$, which can be calculated using the following equation (1).

$$Gm_{neu}=Gm_{soll}-Gm_{alt} \quad (1)$$

In other words, the first (second) phase-encoding gradient applied directly after the refocusing pulse has to generate a gradient moment $Gm_{neu}$ that cancels out the effect of the existing gradient moment $Gm_{alt}$ and additionally generates the resulting (target) gradient moment $Gm_{soll}$.

In a preferred embodiment according to the invention, a further gradient is applied to compensate for VAT ("View Angle Tilting") along the first direction during the selection of the MR data.

Even the gradient moments generated by these further gradients have to be taken into account when the first (or third) phase-encoding gradient is applied according to the variants described above.

In a further preferred embodiment according to the invention, after the acquisition of the MR data relating to a designated k-space line and before the acquisition of a further k-space line, the MR data relating to which are acquired chronologically directly after the MR data relating to the designated k-space line, a further gradient is applied along the third direction in order to cancel out the effect (the gradient moment) of the selection gradient with which the MR data relating to the designated k-space line have been acquired.

As a result of applying the further gradient along the third direction, a "monopolar variant" can be achieved when selecting the k-space lines. In the case of this monopolar variant, the k-space lines are always selected in the same direction or always with a selection gradient that is identical in strength. In contrast to the monopolar variant, the invention also makes provision for a bipolar variant, wherein two chronologically consecutive k-space lines are selected in k-space directions that differ only in strength (that is, anti-parallel directions). The monopolar variant has certain advantages with regard to VAT compensation.

The method according to the invention can be based on both a gradient-echo method and on a spin-echo method, a spin-echo method being preferred.

The present invention also encompasses a magnetic resonance apparatus for the acquisition of MR data relating to a slice of a volume segment within an object of investigation. The magnetic resonance apparatus has a basic field magnet, a gradient field system, one or more RF antennas, and a control computer to control the gradient field system and the RF antenna(s) to receive the measured signals deleted by the RF antenna(s) and to evaluate the test signals, and also to acquire the MR data. The magnetic resonance unit is designed to operate the gradient field system of the magnetic resonance apparatus to apply a first slice selection gradient along a first direction, which is perpendicular to the slice, and, via the one or more RF antennas of the magnetic resonance apparatus to radiate an RF excitation pulse to selectively excite the slice. The control computer is further designed to apply a second slice selection gradient along the first direction, using the gradient field system, and to radiate a refocusing pulse, using the at least one RF antenna, while the second slice selection gradient is applied. Furthermore, the control computer is configured to operate the gradient field system of the magnetic resonance apparatus to apply a first phase-encoding gradient along the first direction and a second phase-encoding gradient along a second direction, which is perpendicular to the first direction. Finally, the control computer is configured to operate the gradient field system of the magnetic resonance apparatus to apply a selection gradient along a third direction, which is perpendicular to the first direction and to the second direction, in order to acquire MR data with the RF antennas while the selection gradient is applied. The control computer is configured to select multiple k-space lines starting from the same refocusing pulse without the RF antenna(s) radiating a further RF pulse.

The advantages of the magnetic resonance apparatus according to the invention essentially correspond to the advantages of the method according to the invention that were described above.

The present invention also encompasses a non-transitory, computer-readable data storage medium encoded with programming instructions, which can be loaded directly into a memory of a programmable control computer or processor of a magnetic resonance apparatus. The programming instructions cause any or all embodiments of the methods according to the invention described above to be implemented by the control computer. The storage medium may possibly require programming means, for example, libraries and auxiliary functions, in order to carry out the relevant embodiments of the method. The programming instructions can be in source code (C++ for example), which still has to be compiled and linked or which only has to be interpreted, or can be in an executable software code that only remains to be loaded into the corresponding computation unit or control device in order to be carried out.

The electronically readable data carrier can be, for example a DVD, a magnetic tape or a USB stick, on which electronically readable control data, in particular software (see above), are stored.

In addition to having a reduced scanning time compared with the prior art, the present invention has the advantage of reduced SAR ("Specific Absorption Rate") exposure since clearly fewer refocusing pulses are required. This is a great advantage, precisely in SEMAC scans, which have a very high SAR.

The present invention is particularly suited to the acquisition of MR data within a volume segment in which or in the vicinity of which a metallic implant is located. The present invention is, of course, not restricted to this preferred field of application since the present invention can be used with magnetic field inhomogeneities in general.

DESCRIPTION OF THE PREFERRED EMBODIMENTS

Figure 1:
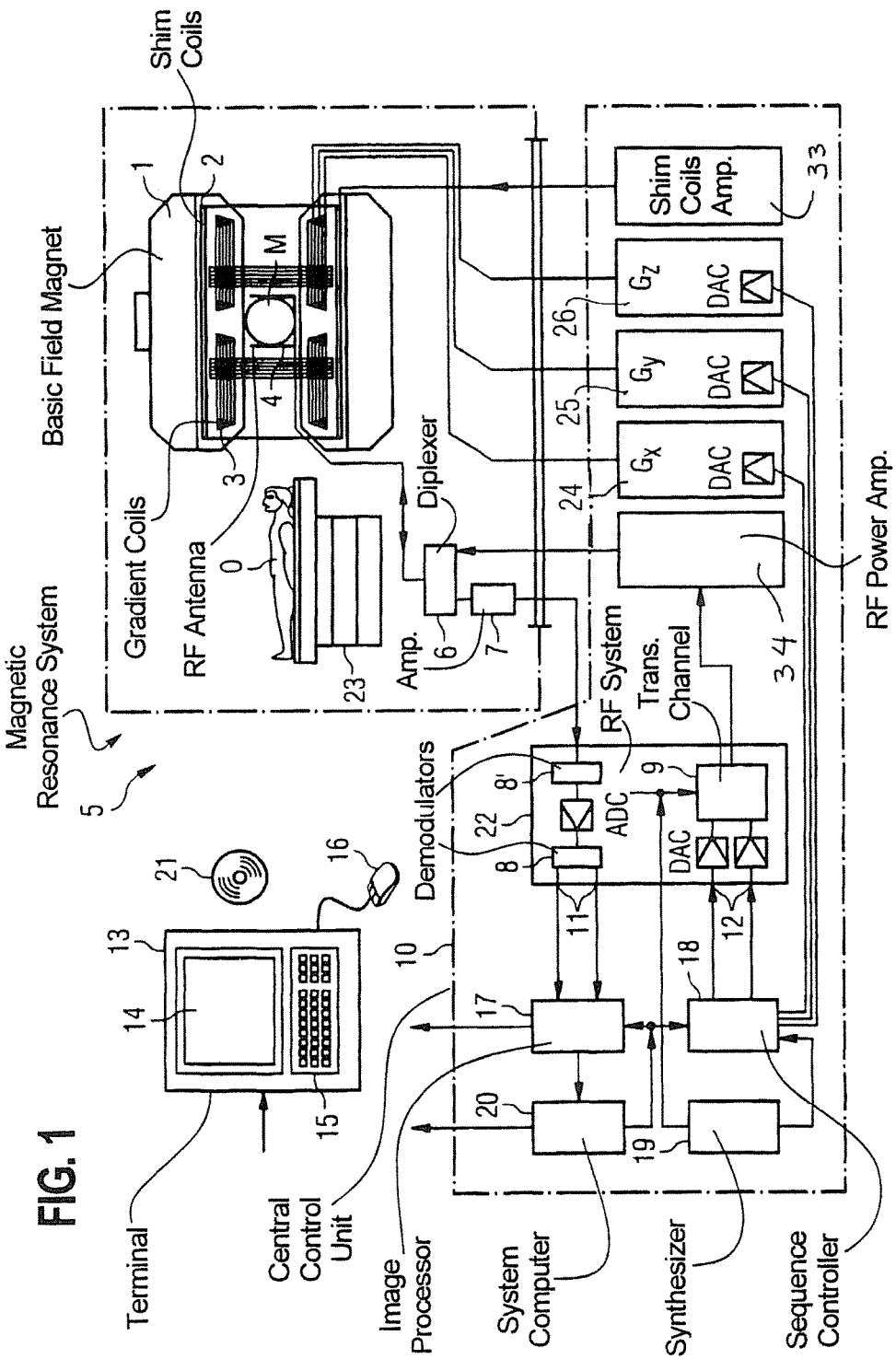
FIG. 1 shows a magnetic resonance apparatus according to the invention.

FIG. 1 is a schematic illustration of a magnetic resonance system 5 (a magnetic resonance imaging or nuclear spin tomography device). Here a basic field magnet 1 generates a strong magnetic field which is constant over time for polarization or orientation of the nuclear spins in an examination region of an object O, such as for example a part to be examined of a human body, which while lying on a table 23 is examined in the magnetic resonance system 5. The high level of homogeneity of the basic magnetic field needed for the nuclear spin resonance measurement is defined in a typically spherical measurement volume M, through which the parts to be examined of the human body are continuously pushed. To support the requirements for homogeneity and in particular to eliminate influences which are invariable over time the so-called shim sheets made of ferromagnetic material are attached at a suitable point. Influences which are variable over time are eliminated by shim coils 2, supplied with currently a shim coils amplifier 33.

A cylindrical gradient field system or gradient field system 3 is employed in the basic field magnet 1, and is composed of three such windings. Each such winding is supplied by an amplifier with current for generating a linear (also variable over time) gradient field in the respective direction of the Cartesian coordinates system. The first partial winding of the gradient field system 3 in this case generates a gradient $G_x$ in the x direction, the second partial winding a gradient $G_y$ in the y direction and the third partial winding a gradient $G_z$ in the z direction. The amplifier has a digital-to-analog converter which is triggered by a sequence controller 18 to generate properly timed gradient pulses.

Located within the gradient field system 3 is one (or more) radio-frequency antennas 4 which convert the radio-frequency pulses emitted by a radio-frequency power amplifier 34 into a magnetic alternating field for exciting the nuclei and orienting the nuclear spins of the object O to be examined or of the region of the object O to be examined. Each radio-frequency antenna 4 has of one or more RF transmitting coils and one or more RF receiving coils in the form of an annular, preferably linear or matrix-shaped, arrangement of component coils. The RF receiving coils of the respective radio-frequency antenna 4 also convert the alternating field emitted by the precessing nuclear spins, i.e. generally the nuclear spin echo signals produced by a pulse sequence comprising one or more radio-frequency pulses and one or more gradient pulses, into a voltage (measurement signal) which is fed via an amplifier 7 to a radio-frequency receiving channel 8 of a radio-frequency system 22. The radio-frequency system 22, which is part of a control device 10 of the magnetic resonance system 5, further has a transmitting channel 9 in which the radio-frequency pulses are generated for the excitation of the magnetic nuclear resonance. In this case the respective radio-frequency pulses are represented digitally in the sequence controller 18 as a sequence of complex numbers on the basis of a pulse sequence predefined by the system processor 20. This sequence of numbers is fed as a real part and an imaginary part via respective inputs 12 to a digital-to-analog converter in the radio-frequency system 22 and from this to a transmitting channel 9. In the transmitting channel 9 the pulse sequences are modulated up to a radio-frequency carrier signal, whose basic frequency corresponds to the resonance frequency of the nuclear spins in the measurement volume.

The switch from transmitting to receiving mode is effected by a transmit/receive diplexer 6. The RF transmitting coils of the radio-frequency antenna(s) 4 radiate the radio-frequency pulses into the measurement volume M to excite the nuclear spins and resulting echo signals are scanned via the RF receiving coil(s). The correspondingly obtained nuclear resonance signals are demodulated on a phase-sensitive basis to an intermediate frequency in the receiving channel 8' (first demodulator) of the radio-frequency system 22, digitized in the analog-to-digital converter (ADC) and emitted via the output 11. This signal is still demodulated to the frequency 0. The demodulation to the frequency 0 and the separation into real and imaginary parts takes place after digitization in the digital domain in a second demodulator 8. Using an image processor 17 an MR image is reconstructed from the measurement data obtained in this manner via an output 11. The administration of the measurement data, the image data and the control programs takes place via the system processor 20. On the basis of a parameter containing control programs the sequence controller 18 controls the generation of the respectively desired pulse sequences and the corresponding scanning of the K space. In particular the sequence controller 18 in this case controls the properly timed switching of the gradients, the transmission of the radio-frequency pulses with defined phase amplitude and the receipt of the nuclear resonance signals. The time basis for the radio-frequency system 22 and the sequence controller 18 is provided by a synthesizer 19. The selection of corresponding control programs for generating an MR image, which are stored for example on a DVD 21, and the display of the generated MR image are effected via a terminal 13 that has a keyboard 15, a mouse 16 and a monitor 14.

Figure 2:
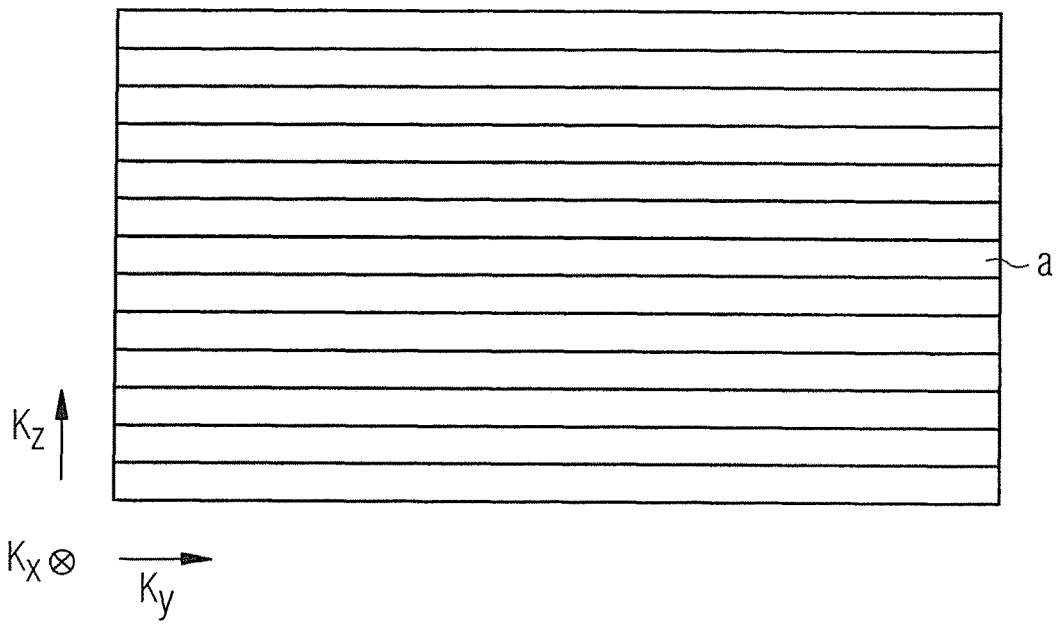
FIG. 2 shows the filling (entry of acquired data into) of k-space according to the SEMAC method.

FIG. 2 shows the sampling of k-space according to the SEMAC method.

The objective is to acquire, where possible, all the spins that are excited by a selective excitation of the slice a. Because of magnetic field inhomogeneities, the spins excited by the selective excitation are located in a volume segment that is at least partially distorted and displaced with respect to the slice a. For this reason, according to the SEMAC method, slices in the $K_z$ direction in the vicinity of the slice a are also sampled or spatially resolved in k-space, as shown in FIG. 2.

Each slice shown in FIG. 2 corresponds to a designated phase-encoding step in the slice selection direction $K_z$, that is, to a designated gradient moment with respect to a first phase-encoding gradient, which is active in the Kz direction. In order to acquire the MR data relating to a slice, a designated number of phase-encoding steps are necessary along a second direction $K_y$. For each of these phase-encoding steps, a k-space line in a third direction $K_x$ is selected, the first direction $K_z$ or slice selection direction, the second direction $K_y$ and the third direction $K_z$ being reciprocally perpendicular to one another.

Figure 3:
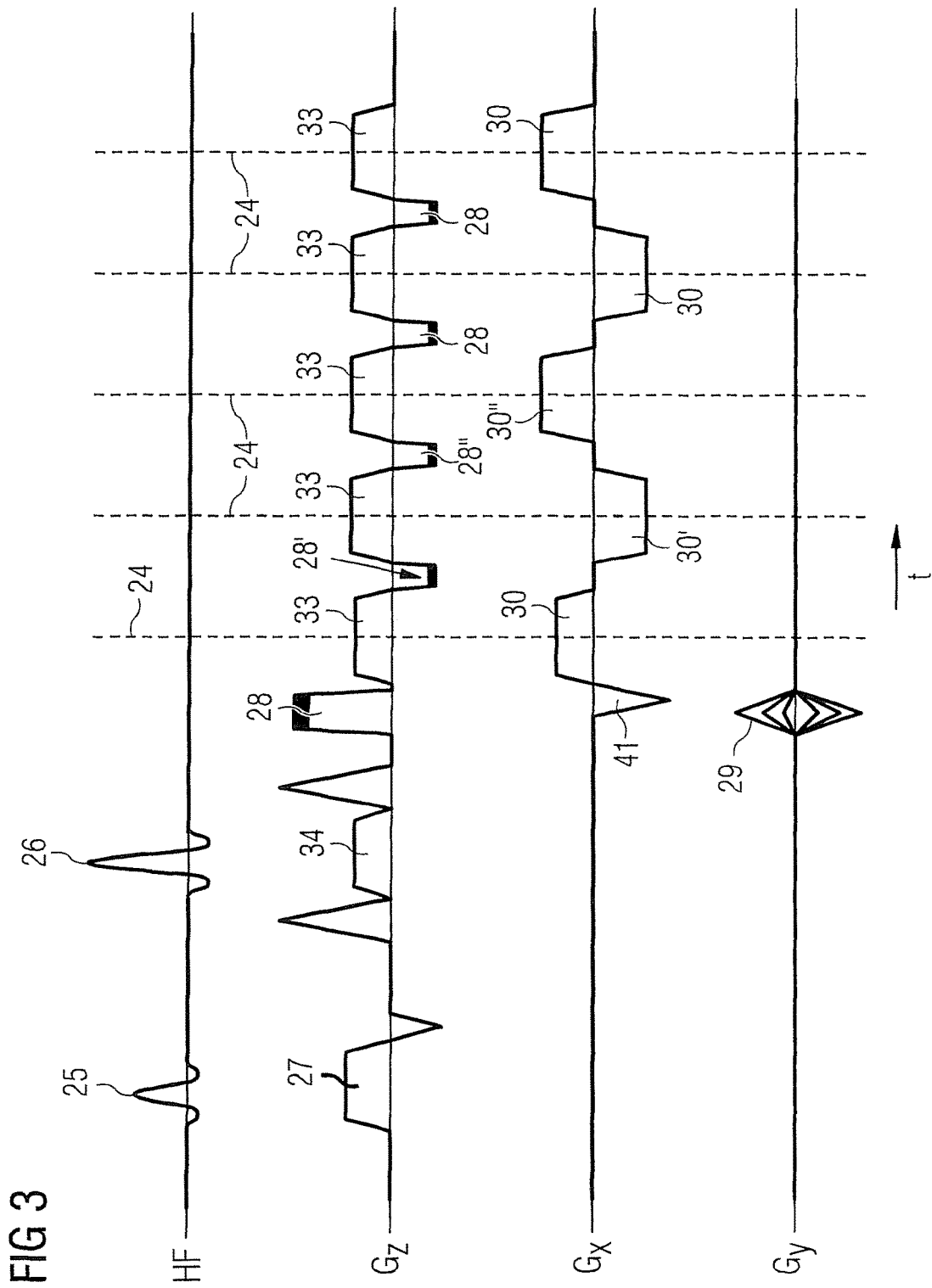
FIG. 3 shows a first variant of a sequence according to the invention that is based on a spin-echo sequence.

FIG. 3 shows a spin-echo sequence for sampling k-space. The slice a is excited using an RF excitation pulse 25, while a slice selection gradient 27 is applied in the slice selection direction $K_z$. Next a refocusing pulse 26 is applied, while a further slice selection gradient 34 is applied in the slice selection direction $K_z$, such that only the spins in the slice a are refocused. A phase encoding then ensues using the first phase-encoding gradient 28 in the slice selection direction and the second phase-encoding gradient 29 along a second direction $K_y$ perpendicular to the slice selection direction $K_z$. By applying the gradient 41 in a third direction $K_x$ perpendicular to the slice selection direction $K_z$ and second direction $K_y$, the selection of the k-space line can start at the beginning of k-space line with the selection gradient 30 applied along the third direction $K_x$. The gradient 33 that is applied during the selection of the MR data serves to compensate for VAT, as described in the SEMAC document cited above. The spin echo 24 appears in the middle of the selection.

After selection of the first k-space line, navigation ensues, by again applying the first phase-encoding gradient 28' in k-space, towards the chronologically next k-space line, which is subsequently selected with the selection gradient 30' applied. In a similar manner, by again applying the first phase-encoding gradient 28", navigation ensues towards the chronologically next k-space line, which is then selected with the selection gradient 30" being applied. The selection of further k-space lines is continued in the manner described until the selection of the MR data is progressed with the radiation of a further RF excitation pulse 25, which is then followed by a further refocusing pulse 26.

Figure 4:
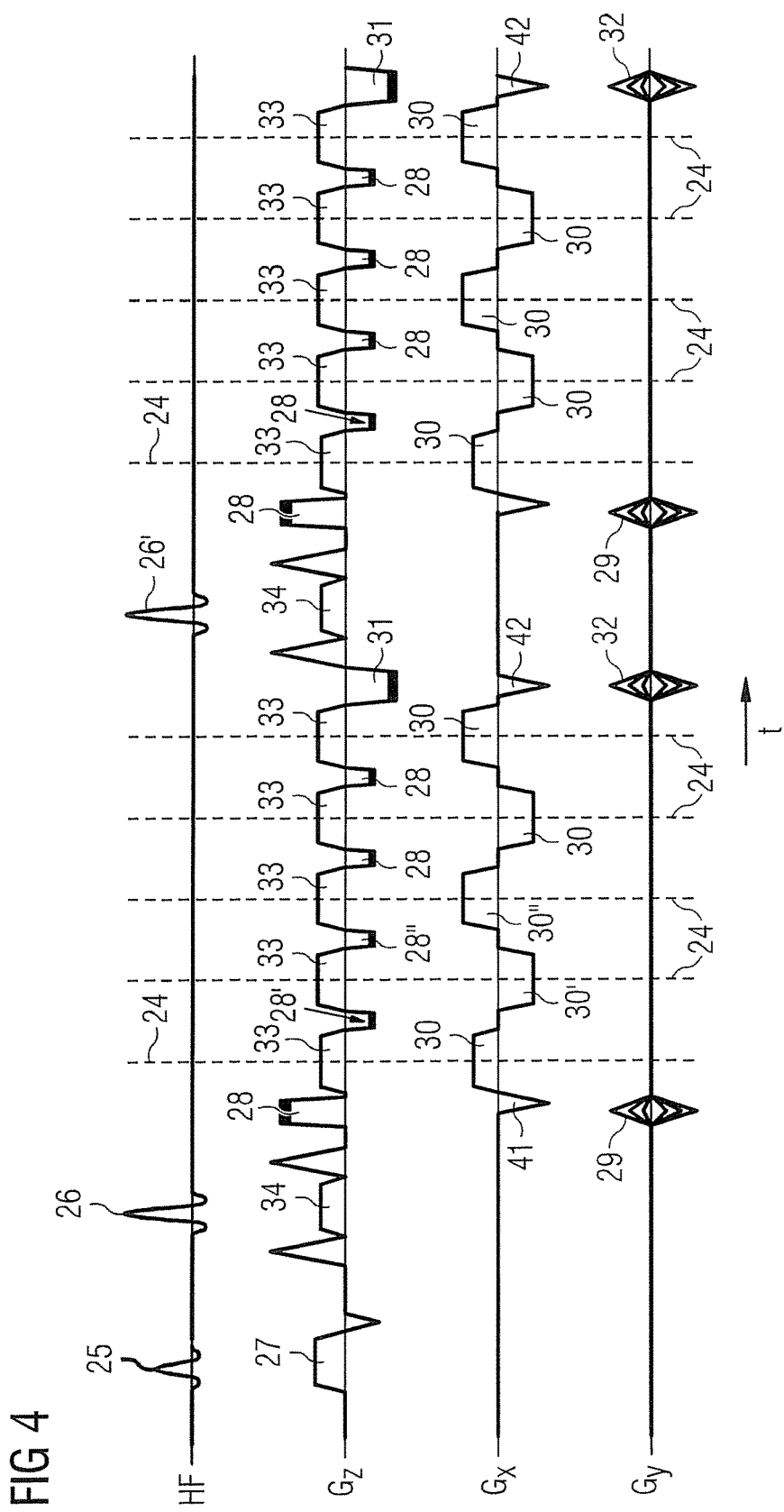
FIG. 4 shows a second variant of a sequence according to the invention that is based on a turbo-spin-echo sequence.

FIG. 4 shows a variant of the spin-echo sequence shown in FIG. 3, in which multiple refocusing pulses 26, 26' are radiated, starting from an RF excitation pulse. Shortly before the second refocusing pulse 26' is radiated, starting from the same RF excitation pulse 25, a third phase-encoding gradient 31 is applied along the first direction $K_z$. The gradient moment generated by this third phase-encoding gradient 31 corresponds in strength to the sum of those gradient moments that have been generated by the gradients 28, 28', 28", 33 along the first direction $K_z$ since the first refocusing pulse 26 was generated. Since the sign in front of the gradient moment generated by the third phase-encoding gradient 31 precisely corresponds with the negative sign in front of the sum of the gradient moments, the gradient moment generated by the third phase-encoding gradient 31 virtually cancels out the effect of the sum of the gradient moments, such that the phase encoding along the first direction $K_z$ corresponds with the phase encoding after the first refocusing pulse 26 has been radiated or with the phase encoding after the RF excitation pulse has been radiated (that is, there is no phase encoding).

In a similar manner, with the fourth phase-encoding gradient 32 along the second direction $K_y$, a gradient moment is generated, which corresponds in strength to the gradient moment generated by the second phase-encoding gradient 29, but is preceded by a sign that is negative thereto. The fourth phase-encoding gradient 32 therefore compensates for the effects of the second phase-encoding gradient 29. Finally, the gradient moment generated by the further gradient 42 along the third direction $K_x$ corresponds in strength with the sum of the gradient moments that have been generated by the gradients 41, 30, 30', 30" along the third direction since the first refocusing pulse 26 was radiated, but is preceded by a sign that is negative thereto. In other words, the further gradient 42 ensures that at the start of the radiation of the second refocusing pulse 26' (and also after the second refocusing pulse 26' has been radiated) there is no phase encoding along the third direction.

In principle, the same gradients are applied after the second refocusing pulse 26' as after the first refocusing pulse 26, in order to acquire further k-space lines according to the SEMAC method.

It should be pointed out that gradients which act chronologically in direct succession in the same direction can also be combined in one gradient. They are only shown separately in FIGS. 3 and 4 only for a more clear explanation.

Figure 5:
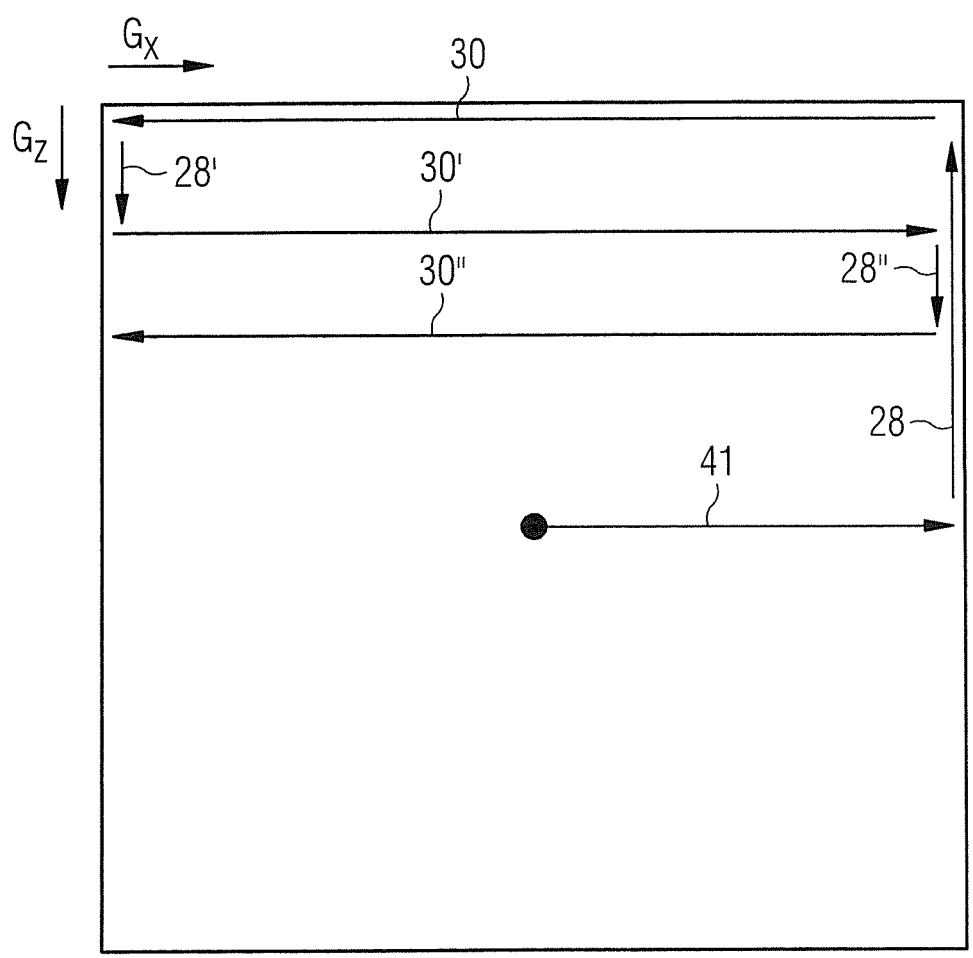
FIG. 5 is a diagram showing how k-space is scanned according to the invention.

FIG. 5 shows in diagram form how k-space is navigated with the aid of the sequences illustrated in FIGS. 3 and 4. By applying the gradient 41 and the first phase-encoding gradient 28, navigation ensues to the start of the k-space line that, chronologically, is to be acquired first. This k-space line is subsequently selected with the selection gradient 30 applied. Navigation subsequently ensues to the next k-space line through a further application of the first phase-encoding gradient 28'. This said k-space line is selected this time in a direction that is anti-parallel to the selection direction of the first k-space line, with the selection gradient 30' being applied. Navigation now ensues in a known manner, through a further application of the first phase-encoding gradient 28", to the start of the next or third k-space line, which line is then selected in the same selection direction as the first k-space line, with the selection gradient 30" being applied.

With the second phase-encoding gradient 29, which is applied before the acquisition of the first k-space line and at the same time as the first phase-encoding gradient 28 and the gradient 41, it is determined as it were, in which x, z-plane perpendicular to the second direction $K_y$, the k-space lines shown in FIG. 5 are acquired.

It should be noted that, through a corresponding variation of the first phase-encoding gradient 28, it is also possible to acquire the k-space lines shown in a different sequence or to acquire other k-space lines.

Figure 6:
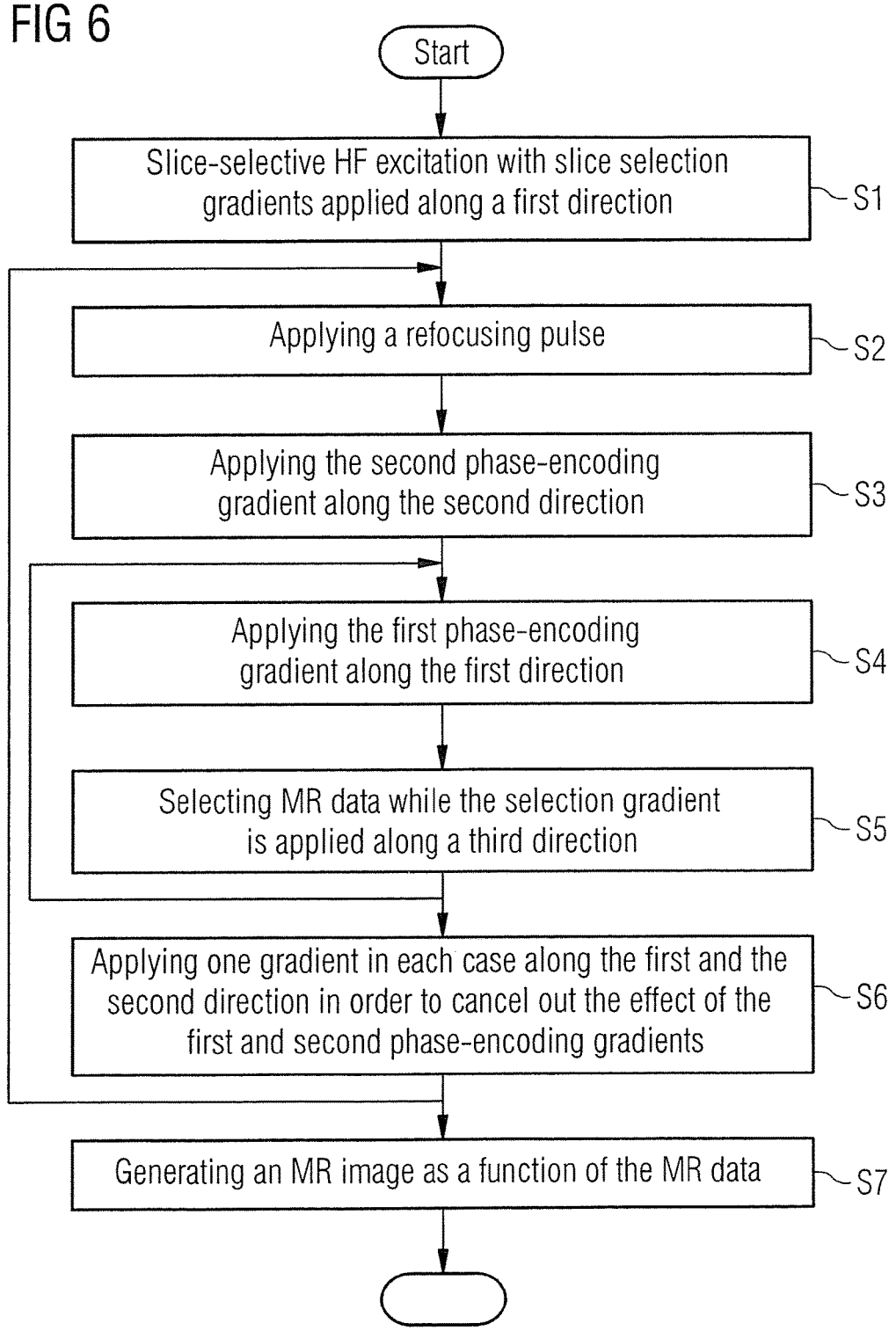
FIG. 6 is a flowchart of a method according to the invention.

FIG. 6 shows the method according to the invention in the form of a flowchart.

In the first step S1, a slice of the predetermined volume segment is selectively excited by radiating the RF excitation pulse 25 with the slice selection gradient 27 being applied. Subsequently, in the second step S2, a refocusing pulse 26 is radiated while a further slice selection gradient 34 is applied along the first direction or slice selection direction $K_z$. In step S3, the second phase-encoding gradient 29 is then applied, this being followed in step S4 by the first phase-encoding gradient 28 being applied along the first direction $K_z$ before, in step S5, the MR data are selected with the selection gradient 30 being applied along the third direction $K_x$. Steps S4 and S5 can be repeated a plurality of times in order to select multiple k-space lines starting from the same refocusing pulse 26.

After a multiple k-space lines have been selected, in step S6 the third phase-encoding gradient 31 is applied in the first direction $K_z$ and the fourth phase-encoding gradient 32 is applied in the second direction $K_y$ in order to cancel out the effect of the gradients 28, 28', 28", 33 or 29 that have been applied in the first direction $K_z$ or in the second direction $K_y$ since the last refocusing pulse 26. The method subsequently reverts to the second step S2 in order to radiate the next refocusing pulse 26' and acquire further k-space lines.

If all the intended k-space lines have not yet been acquired, it is also possible according to the invention to revert to the first step S1 in order to radiate a further layer-selective RF excitation pulse 25. As soon as all the intended k-space lines have been selected, in step 8 one or a plurality of MR images are reconstructed, depending on the MR data that have been acquired.

Although modifications and changes may be suggested by those skilled in the art, it is the intention of the inventor to embody within the patent warranted hereon all changes and modifications as reasonably and properly come within the scope of his contribution to the art.

I claim as my invention:

1. A method for acquisition of magnetic resonance (MR) data from a slice of a predetermined volume of an examination subject while the examination subject is situated in an MR scanner comprising a radio-frequency (RF) antenna arrangement and a gradient coil system, said method comprising:

from a control computer, operating the gradient coil system of the MR scanner to activate a first slice selection gradient along a first direction that is perpendicular to said slice;

from said control computer, operating said RF antenna arrangement of said MR scanner to radiate an RF excitation pulse that selectively excites nuclear spins in said slice;

from said control computer, operating the gradient coil system of said MR scanner to activate a second slice selection gradient along said first direction;

from said control computer, operating said RF antenna arrangement of said MR scanner to radiate a refocusing pulse;

from said control computer, operating said gradient coil system of said MR scanner to activate a first phase encoding gradient along said first direction;

from said control computer, operating said gradient coil system of said MR scanner to activate a second phase encoding gradient along a second direction that is perpendicular to said first direction;

from said control computer, operating said gradient coil system of said MR scanner to activate a selection gradient along a third direction that is perpendicular to each of said first direction and said second direction, and acquiring MR data, resulting from the excited nuclear spins of said slice, while said selection gradient is activated;

from said control computer, entering the acquired MR data into multiple k-space lines in an electronic memory organized as k-space, with each k-space line in said multiple k-space lines being selected starting from said refocusing pulse, without a further RF pulse being radiated; and via said control computer, making said MR data in k-space available from said electronic memory in electronic form, as a data file.

2. A method as claimed in claim 1 comprising selecting said multiple k-space lines starting from said refocusing pulse by:

from said control computer, operating said gradient coil system of said MR scanner to activate said first phase encoding gradient along said first direction; and from said control computer, operating said gradient coil system of said MR scanner to apply said selection gradient along said third direction, and acquiring said MR data while said selection gradient is activated.

3. A method as claimed in claim 1 comprising selecting said multiple k-space lines starting from said refocusing pulse by:

from said control computer, operating said gradient coil system of said MR scanner to activate said second phase encoding gradient along said second direction; and from said control computer, operating said gradient coil system of said MR scanner to apply said selection gradient along said third direction, and acquiring said MR data while said selection gradient is activated.

4. A method as claimed in claim 1 comprising, from said control computer, operating said RF antenna arrangement of said MR scanner to radiate a plurality of refocusing pulses for each RF excitation pulse, and selecting said multiple k-space lines for each refocusing pulse, without radiating further RF pulses.

5. A method as claimed in claim 4 comprising after selecting said multiple k-space lines for a selected one of said refocusing pulses and before radiating a further refocusing pulse chronologically after said selected refocusing pulse, operating said gradient coil system of said MR scanner from said control computer to activate a third phase encoding gradient along said first direction that cancels an effect of any other gradient along said first direction that was activated after said selected refocusing pulse, and to activate a fourth phase encoding gradient along said second direction that cancels an effect of any gradients along said second direction that were activated after said selected refocusing pulse.

6. A method as claimed in claim 4 comprising, after selecting said multiple k-space lines for said selected refocusing pulse and after radiating a further refocusing pulse that chronologically follows directly after said selected focusing pulse, operating said gradient coil system of said MR scanner from said control computer to apply said first phase encoding gradient directly after said first refocusing pulse dependent on an effect of all gradient applied along said first direction after said RF excitation pulse, and activating the second phase encoding gradient directly after said further refocusing pulse dependent on an effect of all gradients applied along said second direction after said RF excitation pulse.

7. A method as claimed in claim 1 comprising, from said control computer, operating said gradient coil system of said MR scanner during acquisition of said MR data to activate a further gradient along said first direction that compensates for view angle tilting.

8. A method as claimed in claim 1 comprising, from said control computer, operating said gradient coil system of said MR scanner, after acquiring MR data for one of said multiple k-space lines and before acquiring MR data for a directly consecutive k-space line in said multiple k-space lines, to activate a further gradient along said third direction that cancels an effect of said selection gradient.

9. A magnetic resonance (MR) apparatus comprising:
an MR scanner comprising a radio-frequency (RF) coil arrangement and a gradient coil system, said MR scanner being adapted to receive an examination subject therein from whom MR data are to be acquired from a slice within a predetermined volume of the examination subject;
a control computer configured to operate the gradient coil system of the MR scanner to activate a first slice selection gradient along a first direction that is perpendicular to said slice;
said control computer being configured to operate said RF antenna arrangement of said MR scanner to radiate an RF excitation pulse that selectively excites nuclear spins in said slice;
said control computer being configured to operate the gradient coil system of said MR scanner to activate a second slice selection gradient along said first direction;
said control computer being configured to operate said RF antenna arrangement of said MR scanner to radiate a refocusing pulse;
said control computer being configured to operate said gradient coil system of said MR scanner to activate a first phase encoding gradient along said first direction;
said control computer being configured to operate said gradient coil system of said MR scanner to activate a second phase encoding gradient along a second direction that is perpendicular to said first direction;
said control computer being configured to operate said gradient coil system of said MR scanner to activate a selection gradient along a third direction that is perpendicular to each of said first direction and said second direction, and acquiring MR data, resulting from the excited nuclear spins of said slice, while said selection gradient is activated;
an electronic memory organized as k-space;
said control computer being configured to enter the acquired MR data into multiple k-space lines in said electronic memory organized as k-space, with each k-space line in said multiple k-space lines being selected starting from said refocusing pulse, without a further RF pulse being radiated; and
said control computer being configured to make said MR data in k-space available from said electronic memory in electronic form, as a data file.

10. A non-transitory, computer-readable data storage medium encoded with programming instructions, said storage medium being loaded into a control computer of a magnetic resonance (MR) apparatus that also comprises an MR scanner comprising a radio-frequency (RF) antenna arrangement and a gradient coils system, said MR scanner being adapted to receive an examination subject therein from whom MR data are to be acquired from a slice within a predetermined volume of the examination subject, and said programming instructions causing said control computer to:
operate the gradient coil system of the MR scanner to activate a first slice selection gradient along a first direction that is perpendicular to said slice;
operate said RF antenna arrangement of said MR scanner to radiate an RF excitation pulse that selectively excites nuclear spins in said slice;
operate the gradient coil system of said MR scanner to activate a second slice selection gradient along said first direction;
operate said RF antenna arrangement of said MR scanner to radiate a refocusing pulse;
operate said gradient coil system of said MR scanner to activate a first phase encoding gradient along said first direction;
operate said gradient coil system of said MR scanner to activate a second phase encoding gradient along a second direction that is perpendicular to said first direction;
operate said gradient coil system of said MR scanner to activate a selection gradient along a third direction that is perpendicular to each of said first direction and said second direction, and acquiring said MR data, resulting from the excited nuclear spins of said slice, while said selection gradient is activated;
enter the acquired said MR data into multiple k-space lines in an electronic memory organized as k-space, with each k-space line in said multiple k-space lines being selected starting from said refocusing pulse, without a further RF pulse being radiated; and
make the acquired said MR data in k-space available from said electronic memory in electronic form, as a data file.

* * * * *